US011647956B2

(12) United States Patent
Feiner

(10) Patent No.: US 11,647,956 B2
(45) Date of Patent: May 16, 2023

(54) ELECTROENCEPHALOGRAM SYSTEM AND METHOD

(71) Applicant: Neurofeedback-Partner GmbH, Baldham (DE)

(72) Inventor: Thomas Feiner, Munich (DE)

(73) Assignee: Neurofeedback-Partner GmbH, Baldham (DE)

( * ) Notice: Subject to any disclaimer, the term of this patent is extended or adjusted under 35 U.S.C. 154(b) by 1459 days.

(21) Appl. No.: 15/925,038

(22) Filed: Mar. 19, 2018

(65) Prior Publication Data
US 2019/0282168 A1 Sep. 19, 2019

(51) Int. Cl.
*A61B 5/00* (2006.01)
*A61B 5/291* (2021.01)

(52) U.S. Cl.
CPC ............ *A61B 5/6835* (2013.01); *A61B 5/291* (2021.01); *A61B 5/6831* (2013.01); *A61B 2562/222* (2013.01)

(58) Field of Classification Search
CPC ..... A61B 5/6835; A61B 5/291; A61B 5/6831; A61B 2562/222; A61B 5/24; A61B 5/25; A61B 5/251; A61B 5/271; A61B 2562/225; A61B 2562/221; A61B 2562/22
See application file for complete search history.

(56) References Cited

U.S. PATENT DOCUMENTS

| | | | |
|---|---|---|---|
| 5,345,934 A | | 9/1994 | Highe et al. |
| 5,479,934 A * | | 1/1996 | Imran .................. A61B 5/0017 607/139 |
| 6,161,030 A * | | 12/2000 | Levendowski ...... A61B 5/6803 607/139 |
| 6,574,513 B1 * | | 6/2003 | Collura .................. A61B 5/291 600/383 |
| 6,708,051 B1 * | | 3/2004 | Durousseau ........... A61B 5/291 600/383 |
| 8,406,841 B2 | | 3/2013 | Lin et al. |
| 8,412,303 B2 | | 4/2013 | Regan et al. |
| 9,345,418 B2 | | 5/2016 | Alkire |
| 2004/0073104 A1 | | 4/2004 | Brun del Re et al. |
| 2009/0105576 A1 * | | 4/2009 | Do ......................... A61B 5/291 600/382 |

(Continued)

FOREIGN PATENT DOCUMENTS

| CA | 2438683 | 8/2002 |
|---|---|---|
| CA | 2379268 | 9/2003 |

(Continued)

*Primary Examiner* — Adam Z Minchella
(74) *Attorney, Agent, or Firm* — Gearhart Law, LLC; David Postolski, Esq

(57) ABSTRACT

Disclosed embodiments provide an electroencephalogram system and method. A novel electrode holder provides multiple net grooves for quick attachment and detachment from an electroencephalogram net. The electrode holder further includes a slot adapted to receive a tab that holds the electrode securely in place. The electrode holder can be configured to operate without gel by using sponges containing water or saline solution that provides moisture for enhancing conductivity. The electrode holder can alternatively be configured to operate with gel by using a tab that keeps the gel in contact with the electrode, for situations that warrant the use of gel instead of water.

21 Claims, 7 Drawing Sheets

(56) References Cited

U.S. PATENT DOCUMENTS

| | | | |
|---|---|---|---|
| 2010/0125190 A1* | 5/2010 | Fadem | A61B 5/6814 600/383 |
| 2015/0282760 A1* | 10/2015 | Badower | A61B 5/6803 600/383 |
| 2017/0127966 A1 | 5/2017 | Wu et al. | |
| 2017/0164862 A1 | 6/2017 | Dolev et al. | |
| 2017/0224278 A1* | 8/2017 | Lukoschek | A61B 5/6843 |
| 2017/0258353 A1* | 9/2017 | Jovanovic | A61B 5/6814 |

FOREIGN PATENT DOCUMENTS

| | | |
|---|---|---|
| CN | 106667481 | 5/2017 |
| WO | 02065904 | 8/2002 |

\* cited by examiner

ELECTROENCEPHALOGRAM SYSTEM AND METHOD

FIELD OF THE EMBODIMENTS

The present invention relates generally to medical equipment, and more particularly, to an electroencephalogram system and method.

BACKGROUND

An electroencephalogram (EEG) detects and records brain wave patterns. Small metal discs with thin wires (electrodes) are placed on the skin, and then provide signals to a computer or other electronic device to record the results. Normal electrical activity in the brain makes a recognizable pattern. Utilizing information provided in an EEG, doctors can identify abnormal patterns that indicate seizures. EEGs can also be used to identify causes of other problems, such as sleep disorders and changes in behavior. They may also be used to evaluate brain activity after a severe head injury or before a heart transplant or liver transplant. Thus, EEGs are an important part of medical diagnostics.

Many types of EEG-electrodes use gel or paste to transmit current from the brain to the EEG signal input circuitry. These solutions have only a limited shelf life and they are not reusable because the electrolytic gels tend to be fragile, sticky, and susceptible to drying out after exposure to air. Furthermore, these types of electrodes utilize strong skin adhesives to ensure that intimate coupling to the body is established. Other types of gel electrodes, such as cup electrodes, require the user to smear electrolytic gel or paste on the electrode and paste and gel go to the skin and hair of the client. Additionally, in order to achieve a good impedance (conductivity) the skin needs to be prepared well with abrasive agents that can also hurt the client. This is a very inconvenient procedure and many clients are not tolerating the procedure at all, as they might be oversensitive, especially very young clients and people with autistic spectrum disorder. It is therefore desirable to have improvements in electroencephalogram systems and methods.

SUMMARY

In one embodiment, there is provided an electrode holder, comprising: an annular shell; a first net groove disposed on a top side of the annular shell; a second net groove disposed on a top side of the annular shell; a slot formed in the annular shell adjacent to a bottom side of the annular shell; and a wire groove formed in the slot.

In another embodiment, the first net groove is oriented perpendicularly to the second net groove.

Another embodiment includes a tab configured and disposed to traverse the slot.

In another embodiment, the tab comprises a handle portion and a tongue portion.

Another embodiment includes an opening formed within the tongue portion.

In another embodiment, the annular shell is comprised of plastic.

In another embodiment, the annular shell is comprised of rubber.

In another embodiment, the annular shell is comprised of neoprene.

Another embodiment includes an annular groove disposed adjacent to the bottom side of the annular shell.

Another embodiment includes an electroencephalogram net comprising: a plurality of cords; a plurality of couplers mechanically coupled to at least two cords of the plurality of cords; a plurality of electrode holders, wherein each electrode holder from the plurality of electrode holders is mechanically coupled to a cord from the plurality of cords; wherein each electrode holder comprises: an annular shell; a first net groove disposed on a top side of the annular shell; a second net groove disposed on a top side of the annular shell; a slot formed in the annular shell adjacent to a bottom side of the annular shell; and a wire groove formed in the slot.

In another embodiment, a subset of the plurality of cords is coupled to a clasp.

Another embodiment includes a chin strap coupled to the clasp.

Another embodiment includes a fastener disposed on the chin strap.

In another embodiment, the fastener comprises a hook-and-loop fastener.

In another embodiment, the annular shell of each electrode holder from the plurality of electrode holders is comprised of plastic.

In another embodiment, the annular shell of each electrode holder from the plurality of electrode holders is comprised of rubber.

In another embodiment, the annular shell of each electrode holder from the plurality of electrode holders is comprised of neoprene.

Another embodiment includes a method of using an electroencephalogram net, wherein the electroencephalogram net comprises a plurality of cords; a plurality of couplers mechanically coupled to at least two cords of the plurality of cords; a plurality of electrode holders, wherein each electrode holder from the plurality of electrode holders is mechanically coupled to a cord from the plurality of cords; wherein each electrode holder comprises: an annular shell; a first net groove disposed on a top side of the annular shell; a second net groove disposed on a top side of the annular shell; a slot formed in the annular shell adjacent to a bottom side of the annular shell; and a wire groove formed in the slot, wherein the method comprises: inserting an electroencephalogram electrode into each electrode holder; and inserting a tab into the slot of each electrode holder.

In another embodiment, inserting a tab comprises inserting a tab with tongue with an opening therein; and inserting a sponge into the annular shell of each holder.

Another embodiment includes performing an ambient vaporization process.

Another embodiment includes inserting gel into the annular shell of each electrode holder, and; wherein inserting a tab comprises inserting a tab with a solid tongue.

The structure, operation, and advantages of disclosed embodiments will become further apparent upon consideration of the following description taken in conjunction with the accompanying figures (FIGs.). The figures are intended to be illustrative, not limiting. Certain elements in some of the figures may be omitted, or illustrated not-to-scale, for illustrative clarity.

DETAILED DESCRIPTION

Disclosed embodiments provide an electroencephalogram system and method. A novel electrode holder provides multiple net grooves for quick attachment and detachment from an electroencephalogram net. The electrode holder further includes a slot adapted to receive a tab that holds the electrode securely in place. The electrode holder can be configured to operate without gel by using sponges containing water or saline solution that provides moisture for enhancing conductivity. The electrode holder can alternatively be configured to operate with gel by using a tab that keeps the gel in contact with the electrode, for situations that warrant the use of gel instead of water.

Figure 1B:
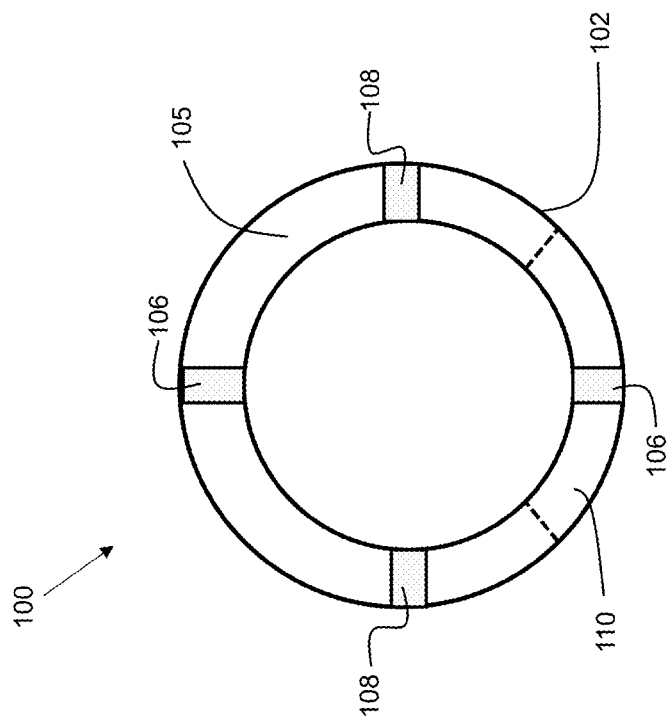
FIG. 1B shows a top-down view of the electrode holder of FIG. 1A.
Figure 1A:
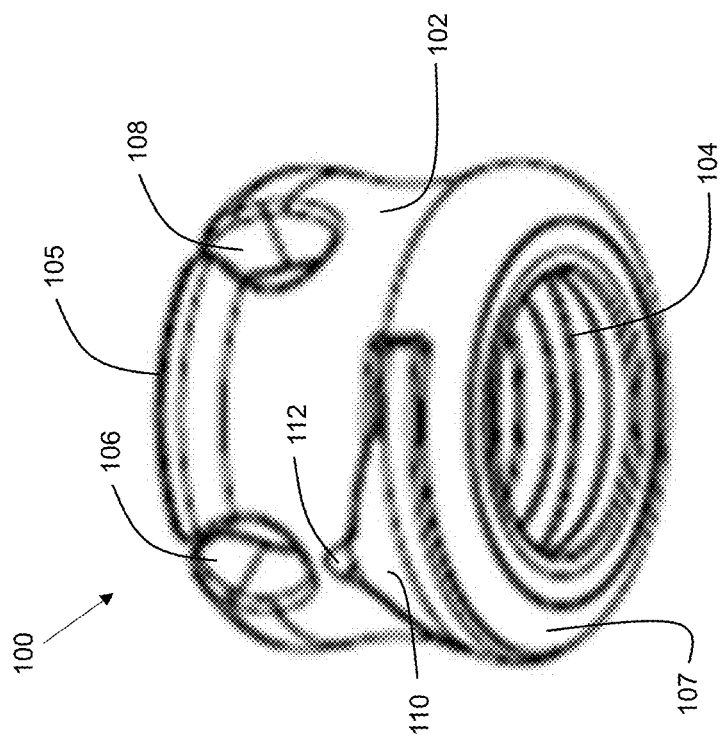
FIG. 1A shows a perspective view of an electrode holder in accordance with embodiments of the present invention.

FIG. 1A shows a perspective view of an electrode holder 100 in accordance with embodiments of the present invention. FIG. 1B shows a top-down view of the electrode holder of FIG. 1A. Electrode holder 100 is comprised of an annular shell 102, which forms cavity 104. The annular shell 102 may be comprised of plastic, rubber, neoprene, or other suitable material(s). A first net groove 106 is disposed on a top side 105 of the annular shell 102. A second net groove 108 is also disposed on the top side 105 of the annular shell 102. As can be seen in FIG. 1B, the first net groove 106 may be oriented perpendicularly to the second net groove 108. The net grooves 106 and 108 are used to mechanically couple the electrode holder 100 to an electroencephalogram net in accordance with embodiments of the present invention.

In use with an electroencephalogram net, the bottom side 107 is oriented towards the skin of a patient, with an electrode placed within cavity 104 such that the electrode receives electrical signals from the skin of the patient. In some embodiments, a sponge containing a saline solution contacts the skin, and the electrode is in contact with the sponge. In other embodiments, a conductive gel is used in place of a sponge. In such embodiments, the conductive gel contacts the skin, and the electrode is placed in the gel. A slot 110 is formed in the sidewall of the annular shell as indicated in FIG. 1A and FIG. 1B. A wire groove 112 is formed in the slot 110 to accommodate an electrode wire. During use, a tab is inserted into the slot 110 to secure an electrode in place within the electrode holder 100. In some embodiments, the annular shell has a diameter in the range from one centimeter to three centimeters.

Figure 2:
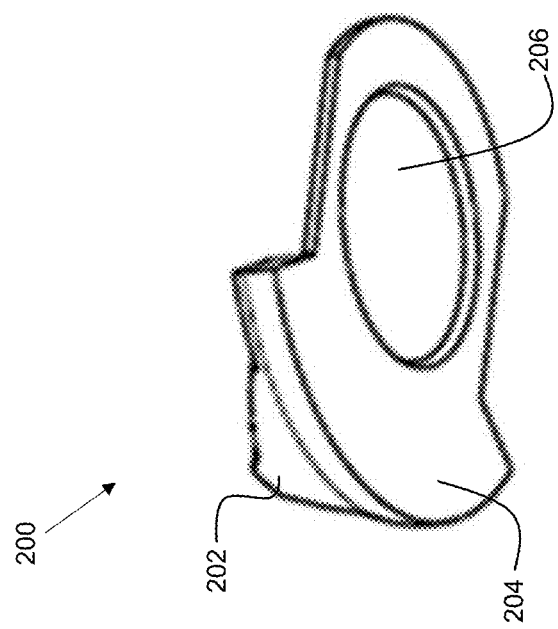
FIG. 2 shows a tab in accordance with embodiments of the present invention.

FIG. 2 shows a tab 200 in accordance with embodiments of the present invention. Tab 200 is configured and disposed to traverse the slot 110 (FIG. 1A). Tab 200 includes a handle portion 202, which is affixed to a tongue portion 204. To prepare an electrode holder for use, an electrode may be first inserted into slot 110 (FIG. 1A). Then, the tab 200 is inserted into the slot, securing the electrode below it. Opening 206 formed within tongue 204 allows ambient vapor to reach the sponge, providing the ability to replenish the sponge moisture during longer measurement sessions.

Figure 3:
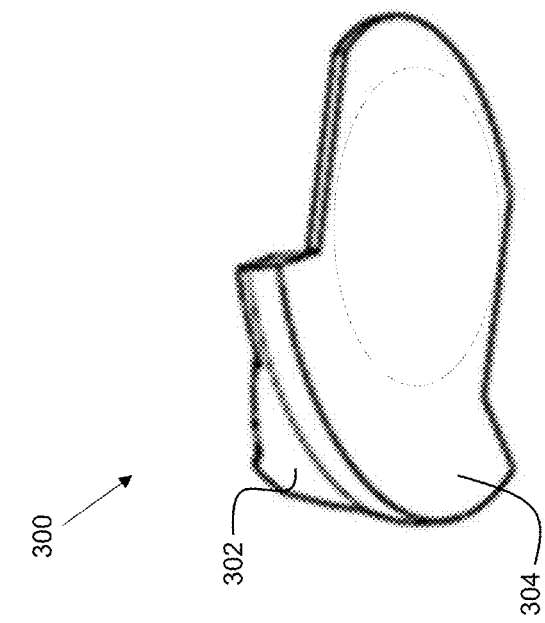
FIG. 3 shows a tab in accordance with alternative embodiments of the present invention.

FIG. 3 shows a tab 300 in accordance with alternative embodiments of the present invention. Tab 300 includes handle portion 302 and tongue portion 304. Tab 300 is similar to tab 200 of FIG. 2, except tab 300 utilizes a solid tongue portion 304, and thus, there is no opening in the tongue (compare with 206 of FIG. 2). In this way, there is more of a seal between the tongue and an electrode. This embodiment may be used when using the electrode holder of disclosed embodiments with gel, since tab 300 keeps more gel in proximity to the electrode.

Figure 4B:
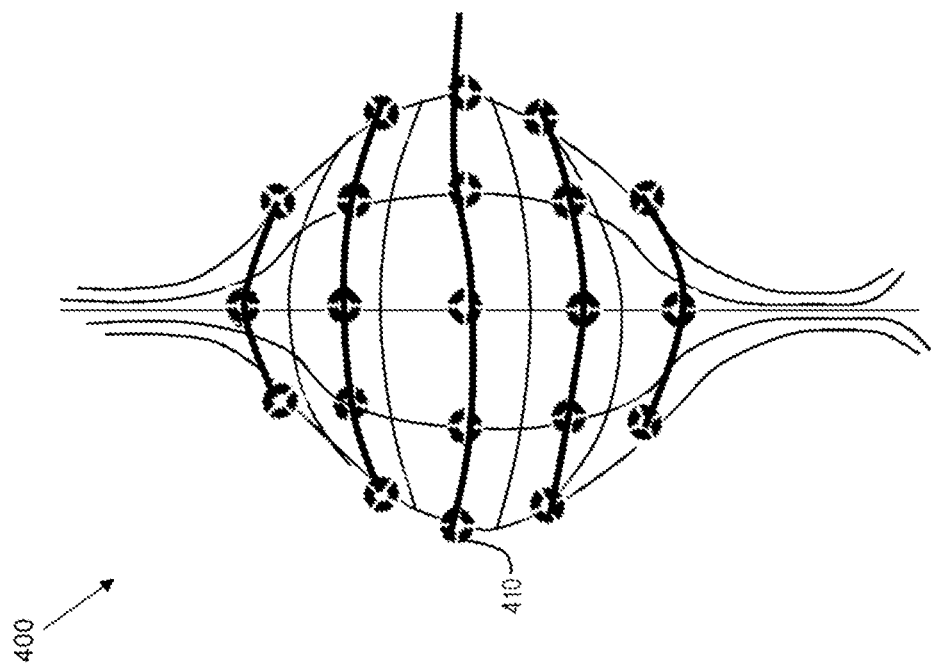
FIG. 4A and FIG. 4B show an electroencephalogram net in accordance with embodiments of the present invention.
Figure 4A:
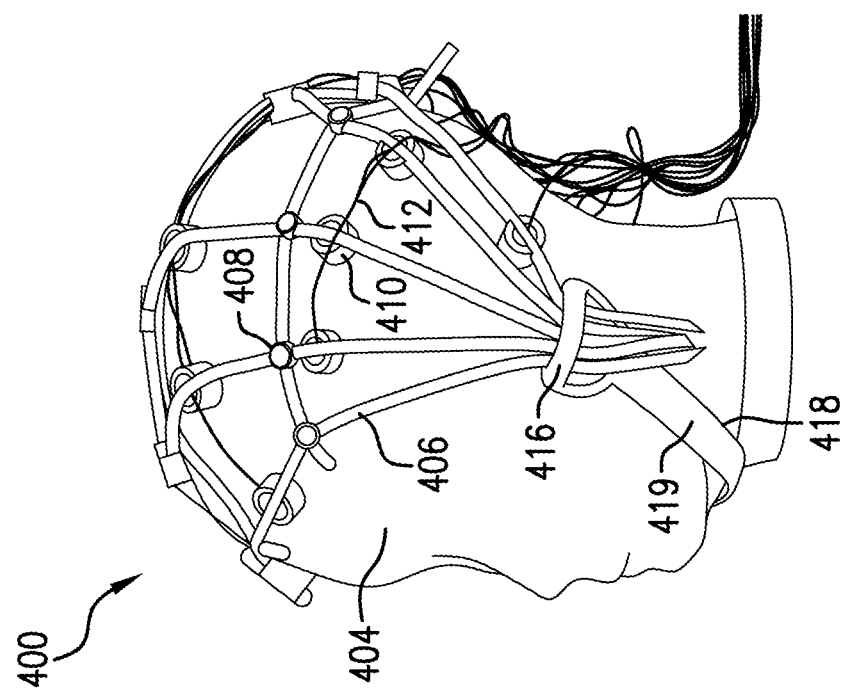
Figure 5:
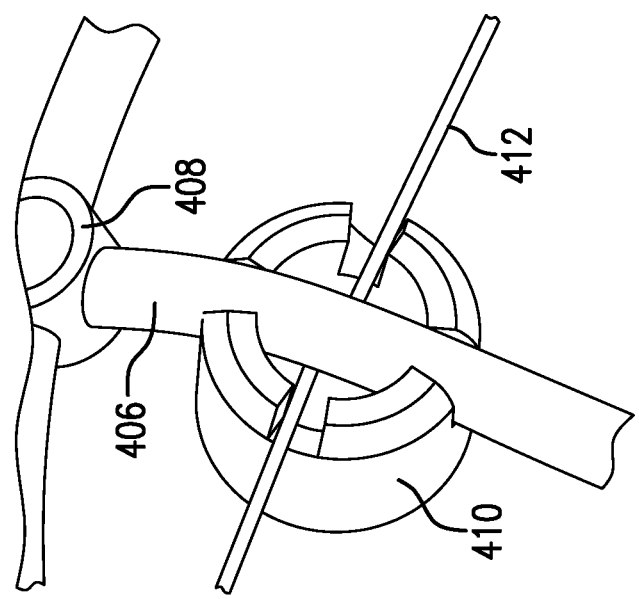
FIG. 5 shows details of the electroencephalogram net of FIG. 4A.

FIG. 4A and FIG. 4B show an electroencephalogram net 400 in accordance with embodiments of the present invention. FIG. 5 shows details of the electroencephalogram net of FIG. 4A. A plurality of cords 406 are arranged in a grid-like pattern to form an electroencephalogram net. In embodiments, the cords may be comprised of rubber, nylon, latex tubes, or other suitable material. To form the grid-like pattern, a plurality of couplers 408 secure two or more cords together. In embodiments, the couplers 408 are cylindrical and have a plurality of holes in the sidewalls for cords to traverse in order to form the net, as visible in FIG. 5.

A plurality of electrode holders, indicated generally as 410, are affixed to the electroencephalogram net by inserting a cord 406 into a net groove (e.g. 106 of FIG. 1A). The electrode holder 410 forms a friction fit with the cord 406. An electrode wire 412 may traverse the perpendicularly oriented net groove (e.g. 108 of FIG. 1A), and be routed underneath the cord 406, and connected to an electrode within the holder 410 and/or an electrode on a different holder within the electroencephalogram net.

Figure 4C:
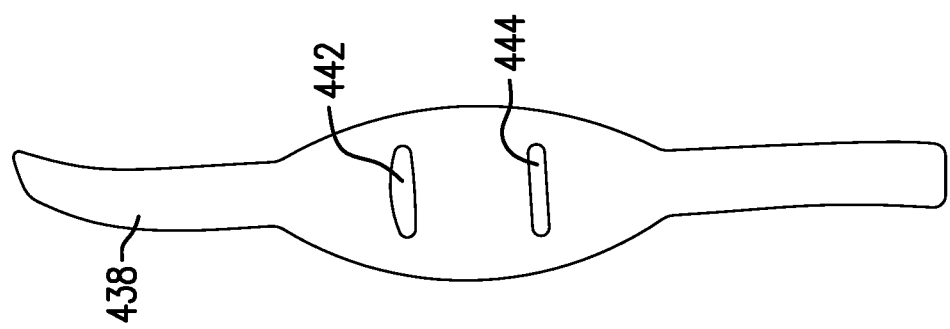
FIG. 4C shows a chin strap in accordance with alternative embodiments of the present invention.

In embodiments, a subset of the plurality of cords is coupled to a clasp 416. Embodiments can further include a chin strap 418 coupled to the clasp 416. In embodiments, a similar clasp (not visible in FIG. 4) is utilized on the other side of the head of the patient. Embodiments can further include a fastener 419 disposed on the chin strap 418. In embodiments, the fastener comprises a hook-and-loop fastener, such as Velcro™. The chin strap 418 can serve to provide force on the cords 406 to ensure sufficient contact with electrodes in the holders 410 and the skin of the patient 404. FIG. 4C shows a chin strap 438 in accordance with alternative embodiments of the present invention. Two slots 442 and 444 can be used to affix additional padding to the chin strap 438 for comfort of the patient.

Figure 6:
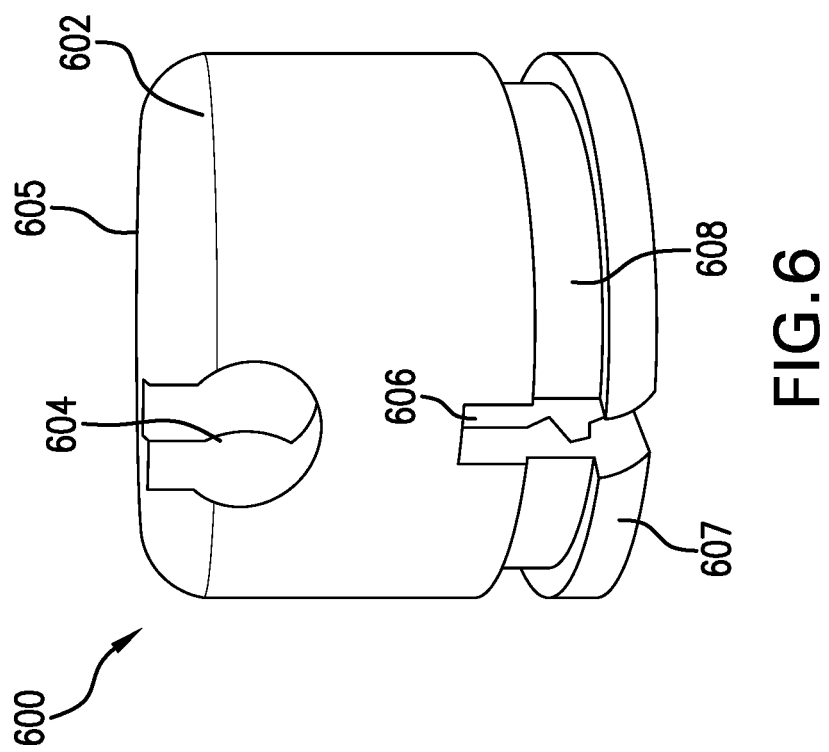
FIG. 6 shows an electrode holder in accordance with alternative embodiments of the present invention.

FIG. 6 shows an electrode holder 600 in accordance with alternative embodiments of the present invention. The electrode holder 600 comprises an annular shell 602, and a net groove 604 disposed on a top side 605 of the annular shell 602. Electrode holder 600 further includes an annular groove 608 disposed adjacent to the bottom side 607 of the annular shell 602. The annular groove 608 allows electrode holder 600 to be compatible with a variety of other electroencephalogram nets that have openings formed therein to secure an electrode holder. A wire groove 606 may be formed within the annular shell 602 to accommodate an electrode wire. In some embodiments, electrode holder 600 may be fabricated using a 3D printing process.

Figure 7:
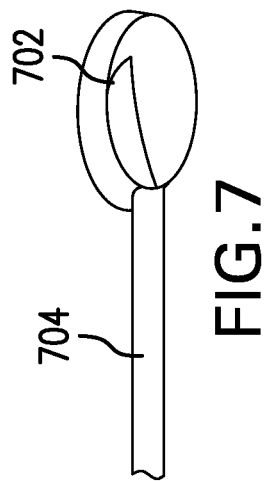
FIG. 7 shows an exemplary electroencephalogram electrode used in embodiments of the present invention.

FIG. 7 shows an exemplary electroencephalogram electrode 702 used in embodiments of the present invention. An electrode wire 704 is used to convey signals from the electrode 702 to an input interface of an electronic device such as a computer, in order to obtain the electroencephalogram.

Figure 8:
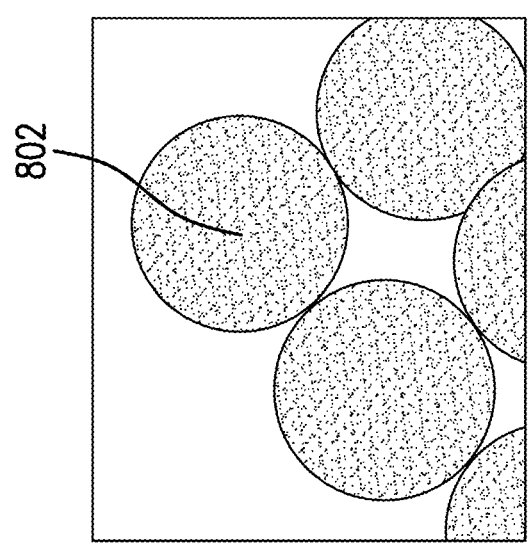
FIG. 8 shows an exemplary sponge used in embodiments of the present invention.

FIG. 8 shows an exemplary sponge 802 used in embodiments of the present invention. The sponge 802 is preferably round and of a size to fit securely within the annular shell of an electrode holder of embodiments of the present invention. In use, water and/or saline solution may be applied to sponge 802.

This embodiment provides various advantages in terms of patient convenience. Usually it takes a shower to get rid of paste and gel after an EEG session. With disclosed embodiments, this is not necessary because of the sponges. There is no extra cleaning or extra hairstyling that is necessary. The electroencephalogram net of disclosed embodiments and the sponges allow preservation of styling and no one sees that there was an EEG done prior. Busy people who do not have much time can just receive their training or measurement without the inconvenience of extra cleanup. Thus, embodiments can include inserting a tab with a tongue having an opening therein, and inserting a sponge into the annular shell of each holder.

Embodiments can further include performing an ambient vaporization process. In this process vapor may be applied within the room where the patient is undergoing a measurement, or in close proximity to the patient, as so to replenish moisture to the sponges. This can be useful for longer measurements, allowing the moisture to be replenished while avoiding the need for gel.

Alternative embodiments can further include inserting gel into the annular shell of each holder, and inserting a tab with a solid tongue. This embodiment utilizes gel, which may be desirable in certain cases, such as for extended duration measurements, or if sponges are not available (e.g. in a home use setting).

Figure 9:
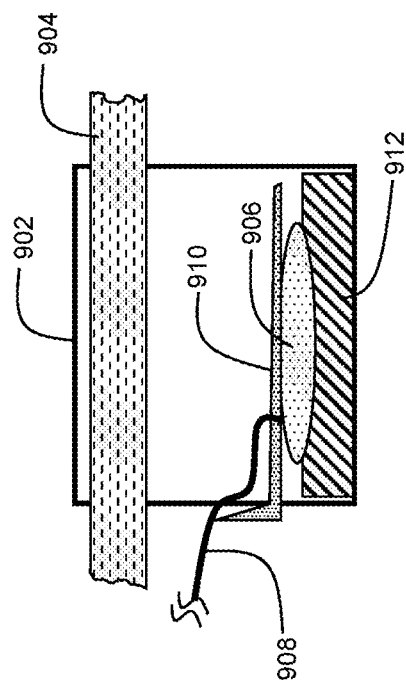
FIG. 9 shows an example of an electrode holder in a gel-free configuration.

FIG. 9 shows an example of an electrode holder 902 in a gel-free configuration. The electrode holder 902 is mechanically coupled to a cord 904. An electrode 906 is placed in the holder, and the electrode wire 908 is routed through a wire groove (e.g. 112 of FIG. 1A). A tab 910 is inserted into the slot (e.g. 110 of FIG. 1A) of the electrode holder 902. A sponge 912 soaked with water and/or saline solution is disposed in the holder 902. Sponge 912 may be similar to sponge 802 of FIG. 8. In embodiments, tab 910 may be similar to tab 200 of FIG. 2, and include an opening to allow moisture from ambient vapor to pass through to the sponge 912 to replenish moisture during longer measurement periods.

Figure 10:
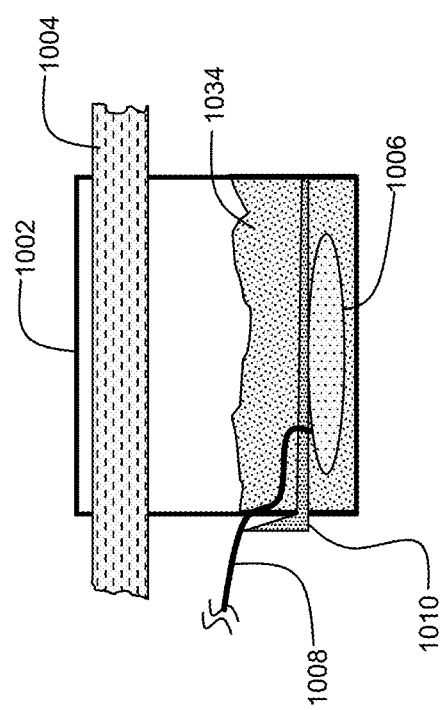
FIG. 10 shows an example of an electrode holder in a gel configuration.

FIG. 10 shows an example of an electrode holder 1002 in a gel configuration. The electrode holder 1002 is mechanically coupled to a cord 1004. An electrode 1006 is placed in the holder, and the electrode wire 1008 is routed through a wire groove (e.g. 112 of FIG. 1A). Gel 1034 is applied within the electrode holder 1002. The tab 1010 is then inserted into the slot (e.g. 110 of FIG. 1A) of the electrode holder 1002. In embodiments, tab 1010 may be similar to tab 300 of FIG. 3, and include a solid tongue to trap some of gel 1034 in contact with the electrode 1006.

As can now be appreciated, disclosed embodiments provide improvements in electroencephalogram systems and methods. A novel electrode holder provides reliable contact for EEG electrodes against the skin of a patient. Grooves in the electrode holder mechanically engage with cords that form an EEG net. An electrode holder may be easily removed for replacement of the holder and/or electrode as needed. Additionally, the electrode holder of disclosed embodiments allows operation in a gel-free mode. Gel free operation provides advantages in terms of convenience. Dry electrodes are quite expensive, but with the electrode holder of disclosed embodiments, a "wet" electrode can be used since the electrode holder is adapted to receive a sponge containing water or saline solution. This provides a gel-free solution at a reduced cost, serving to lower overall medical care costs. The electrode holder of disclosed embodiments can also be configured to work with gels, in cases where use of such a gel is desirable. Thus, disclosed embodiments improve the comfort and convenience of patients who need to undergo an electroencephalogram.

The terminology used herein is for describing particular aspects only and is not intended to be limiting of the invention. As used herein, the singular forms "a", "an" and "the" are intended to include the plural forms as well, unless the context clearly indicates otherwise. It will be further understood that the terms "include" and "including" when used in this specification, specify the presence of stated features, integers, steps, operations, elements, and/or components, but do not preclude the presence or addition of one or more other features, integers, steps, operations, elements, components, and/or groups thereof. Certain examples and elements described in the present specification, including in the claims and as illustrated in the figures, may be distinguished or otherwise identified from others by unique adjectives (e.g. a "first" element distinguished from another "second" or "third" of a plurality of elements, a "primary" distinguished from a "secondary" one or "another" item, etc.) Such identifying adjectives are generally used to reduce confusion or uncertainty, and are not to be construed to limit the claims to any specific illustrated element or embodiment, or to imply any precedence, ordering or ranking of any claim elements, limitations or process steps.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. An electrode holder, comprising: an annular shell; a first cord of an electroencephalogram net; a second cord of the electroencephalogram net; a first net groove disposed on a top side of the annular shell;

wherein the first net groove traverses a diameter of the annular shell in a first orientation;

wherein the first net groove includes a first open proximate groove, radially traversing the top side and creating a first proximate opening in the top side, and a first open distal groove, radially traversing the top side, and creating a first distal opening in the top side, the first open proximate groove opposing the first open distal groove;

wherein the first open proximate groove and the first open distal groove both are open to, and adapted to receive, insertion of the first cord of the electroencephalogram net, in which insertion of the first cord includes the first cord traversing the first proximate opening, resting in the first open proximate groove, traversing the first distal opening, resting in the first distal opening, and traversing the diameter;

a second net groove disposed on the top side of the annular shell;

wherein the second net groove traverses the diameter of the annular shell in a second orientation;

wherein the second net groove includes a second open proximate groove, radially traversing the top side and creating a second proximate opening in the top side, and a second open distal groove, radially traversing the top side, and creating a second distal opening in the top side, the second open proximate groove opposing second first open distal groove, wherein the second open proximate groove and the second open distal groove both are open to, and adapted to receive, insertion of the second cord of the electroencephalogram net, in which insertion of the second cord includes the second cord traversing the second proximate opening, resting in the second open proximate groove, traversing the second distal opening, resting in the second distal opening, and traversing the diameter;

a slot formed in the annular shell adjacent to a bottom side of the annular shell;

wherein the slot forms a slot cavity cross-sectionally traversing the annular shell across the diameter in a cross sectional orientation; the slot creates a slot opening in the annular shell having a slot opening orientation substantially perpendicular to the cross-sectional orientation; and a wire groove formed in the slot.

2. The electrode holder of claim 1, wherein the first net groove is oriented perpendicularly to the second net groove.

3. The electrode holder of claim 1, further comprising a tab configured and disposed to traverse the slot.

4. The electrode holder of claim 3, wherein the tab comprises a handle portion and a tongue portion.

5. The electrode holder of claim 4, further comprising an opening formed within the tongue portion.

6. The electrode holder of claim 1, wherein the annular shell is comprised of plastic.

7. The electrode holder of claim 1, wherein the annular shell is comprised of rubber.

8. The electrode holder of claim 1, wherein the annular shell is comprised of neoprene.

9. The electrode holder of claim 1, further comprising an annular groove disposed adjacent to the bottom side of the annular shell.

10. An electroencephalogram net comprising:
a plurality of cords;
a plurality of couplers mechanically coupled to at least two cords of the plurality of cords;
a plurality of electrode holders, wherein each electrode holder from the plurality of electrode holders is mechanically coupled to a cord from the plurality of cords;
wherein each electrode holder comprises:
an annular shell;
a first net groove disposed on a top side of the annular shell;
wherein the first net groove traverses a diameter of the annular shell in a first orientation;
wherein the first net groove includes a first open proximate groove, radially traversing the top side and creating a first proximate opening in the top side, and a first open distal groove, radially traversing the top side, and creating a first distal opening in the top side, the first open proximate groove opposing the first open distal groove,
wherein the first open proximate and the first open distal groove both are open to, and adopted to receive, insertion of a first cord of the electroencephalogram net, in which insertion of the first cord includes the first cord traversing the first proximate opening, resting in the first open proximate groove, traversing the first distal opening, resting in the first distal opening, and traversing the diameter;
a second net groove disposed on the top side of the annular shell;
wherein the second net groove traverses the diameter of the annular shell in a second orientation;
wherein the second net groove includes a second open proximate groove radially traversing the top side and creating a second proximate opening in the top side, and a second open distal groove, radially traversing the top side, and creating a second distal opening in the top side, the second open proximate groove opposing second first open distal groove,
wherein the second open proximate groove and the second open distal groove both are open to, and adapted to receive, insertion of a second cord of the electroencephalogram net, in which insertion of the second cord includes the second cord traversing the second proximate opening, resting in the second open proximate groove, traversing the second distal opening, resting in the second distal opening, and traversing the diameter;
a slot formed in the annular shell adjacent to a bottom side of the annular shell;
wherein the slot forms a slot cavity cross-sectionally traversing the annular shell across the diameter in a cross sectional orientation; the slot creates a slot opening in the annular shell having a slot opening orientation substantially perpendicular to the cross-sectional orientation; and
a wire groove formed in the slot.

11. The electroencephalogram net of claim 10, wherein a subset of the plurality of cords is coupled to a clasp.

12. The electroencephalogram net of claim 11, further comprising a chin strap coupled to the clasp.

13. The electroencephalogram net of claim 12, further comprising a fastener disposed on the chin strap.

14. The electroencephalogram net of claim 13, wherein the fastener comprises a hook-and-loop fastener.

15. The electroencephalogram net of claim 10, wherein the annular shell of each electrode holder from the plurality of electrode holders is comprised of plastic.

16. The electroencephalogram net of claim 10, wherein the annular shell of each electrode holder from the plurality of electrode holders is comprised of rubber.

17. The electroencephalogram net of claim 10, wherein the annular shell of each electrode holder from the plurality of electrode holders is comprised of neoprene.

18. A method of using an electroencephalogram net, wherein the electroencephalogram net comprises a plurality of cords;
a plurality of couplers mechanically coupled to at least two cords of the plurality of cords;
a plurality of electrode holders, wherein each electrode holder from the plurality of electrode holders is mechanically coupled to a cord from the plurality of cords;
wherein each electrode holder comprises:
an annular shell;
a first net groove disposed on a top side of the annular shell;
wherein the first net groove traverses a diameter of the annular shell in a first orientation;
wherein the first net groove includes a first open proximate groove, radially traversing the top side and creating a first proximate opening in the top side, and a first open distal groove, radially traversing the top side, and creating a first distal opening in the top side, the first open proximate groove opposing the first open distal groove;

wherein the first open proximate groove and the first open distal groove both are open to, and adapted to receive, insertion of a first cord of the electroencephalogram net, in which insertion of the first cord includes the first cord traversing the first proximate opening, resting in the first open proximate groove, traversing the first distal opening, resting in the first distal opening, and traversing the diameter;

a second net groove disposed on the top side of the annular shell;

wherein the second net groove traverses the diameter of the annular shell in a second orientation;

wherein the second net groove includes a second open proximate groove, radially traversing the top side and creating a second proximate opening in the top side, and a second open distal groove, radially traversing the top side, and creating a second distal opening in the top side, the second open proximate groove opposing second first open distal groove;

wherein the second open proximate groove and the second open distal groove both are open to, and adapted to receive, insertion of a second cord of the electroencephalogram net, in which insertion of the second cord includes the second cord traversing the second proximate opening, resting in the second open proximate groove, traversing the second distal opening, resting in the second distal opening, and traversing the diameter;

a slot formed in the annular shell adjacent to a bottom side of the annular shell;

wherein the slot forms a slot cavity cross-sectionally traversing the annular shell across the diameter in a cross sectional orientation; the slot creates a slot opening in the annular shell having a slot opening orientation substantially perpendicular to the cross-sectional orientation; and a wire groove formed in the slot, wherein the method comprises:

inserting an electroencephalogram electrode into each electrode holder; and inserting a tab into the slot of each electrode holder.

19. The method of claim 18, wherein inserting a tab comprises inserting a tab with tongue with an opening therein; and inserting a sponge into the annular shell of each holder.

20. The method of claim 19, further comprising, performing an ambient vaporization process.

21. The method of claim 18, further comprising inserting gel into the annular shell of each electrode holder, and;

wherein inserting a tab comprises inserting a tab with a solid tongue.

* * * * *